US006929681B2

(12) United States Patent
Maleeny et al.

(10) Patent No.: US 6,929,681 B2
(45) Date of Patent: Aug. 16, 2005

(54) AIR SCENTING COMPOSITIONS AND PROCESSES FOR USE THEREOF IN AIR SCENTING DEVICES

(75) Inventors: Robert Maleeny, Ramsey, NJ (US); Kevin Vick, Thomasville, GA (US); James Kinney, Ramsey, NJ (US); David Ziser, Pompton Plains, NJ (US); Richard Laky, Clifton, NJ (US)

(73) Assignee: Scentco, LLC, Thomasville, GA (US)

( * ) Notice: Subject to any disclaimer, the term of this patent is extended or adjusted under 35 U.S.C. 154(b) by 110 days.

(21) Appl. No.: 10/603,554

(22) Filed: Jun. 25, 2003

(65) Prior Publication Data

US 2004/0094037 A1 May 20, 2004

Related U.S. Application Data

(63) Continuation of application No. 09/994,231, filed on Nov. 27, 2001, now abandoned.

(51) Int. Cl.[7] ............................. A61L 9/04; B01D 46/00
(52) U.S. Cl. .......................... 95/285; 96/222; 422/124; 512/2; 55/524
(58) Field of Search ................................ 422/123, 124; 96/222; 95/285; 55/524; 512/2, 4; 428/905; 523/102; 424/76.3, 76.4

(56) References Cited

U.S. PATENT DOCUMENTS

| 2,871,526 A | 2/1959 | Bulloff |
| 3,994,439 A | 11/1976 | Van Breen et al. |
| 4,065,262 A | 12/1977 | Petroff |
| 4,095,031 A | 6/1978 | Engle |
| 4,102,656 A | 7/1978 | Koritz |
| 4,118,226 A | 10/1978 | Bourass |
| 4,159,672 A | 7/1979 | Garguilo et al. |
| 4,257,787 A | 3/1981 | Taylor |
| 4,523,870 A | 6/1985 | Spector |
| 4,563,333 A | 1/1986 | Frigon |
| 4,587,129 A | 5/1986 | Kliment |
| 4,603,030 A | 7/1986 | McCarthy |
| 4,604,114 A | 8/1986 | Ward |
| 4,735,358 A | 4/1988 | Morita et al. |
| 4,903,583 A | 2/1990 | Frazier |
| 4,906,488 A * | 3/1990 | Pera ........................... 426/573 |
| 4,959,087 A | 9/1990 | Kappernaros |
| 4,988,744 A | 1/1991 | Yamamoto |
| 5,034,222 A | 7/1991 | Kellett et al. |
| 5,063,256 A | 11/1991 | Hoshino et al. |
| 5,078,046 A | 1/1992 | Mascolo et al. |
| 5,087,273 A | 2/1992 | Ward |
| 5,240,653 A | 8/1993 | Ramkissoon |
| 5,273,690 A | 12/1993 | McDowell |
| 5,297,988 A | 3/1994 | Nishino et al. |
| 5,324,490 A | 6/1994 | Vlahakis et al. |
| 5,417,929 A | 5/1995 | Kita |
| 5,547,636 A | 8/1996 | Vick et al. |
| 5,587,153 A * | 12/1996 | Angelone et al. ............. 424/66 |
| 5,698,166 A | 12/1997 | Vick et al. |
| 5,985,821 A * | 11/1999 | Dobler et al. .................. 512/2 |
| 6,117,218 A | 9/2000 | Snyder et al. |
| 6,325,475 B1 | 12/2001 | Hayes et al. |
| 6,339,897 B1 | 1/2002 | Hayes et al. |
| 6,379,242 B1 | 4/2002 | Wiseman et al. |
| 6,390,453 B1 | 5/2002 | Frederickson et al. |
| 6,749,672 B2 * | 6/2004 | Lynn ........................... 96/222 |
| 2001/0035095 A1 | 11/2001 | Canfield |

OTHER PUBLICATIONS

Internet Document: "ETI AromaGel, Waterbased Fragrance Gel", http://www.eti-usa/aroma-gel/aroma3.htm#Sparkle%20Powder:, 2002.

* cited by examiner

*Primary Examiner*—Frank M. Lawrence
(74) *Attorney, Agent, or Firm*—Jones Day

(57) ABSTRACT

Disclosed are compositions, processes and devices for use in HVAC systems to provide air freshening scent to air circulating in the system.

26 Claims, 2 Drawing Sheets

AIR SCENTING COMPOSITIONS AND PROCESSES FOR USE THEREOF IN AIR SCENTING DEVICES

This is a continuation application of application Ser. No. 09/994,231, filed Nov. 27, 2001, now abandoned.

BACKGROUND OF THE INVENTION

1. Field of the Invention

The present invention relates generally to air scenting compositions and to processes for use of such compositions in air scenting devices as well as to devices produced utilizing such compositions. More particularly, it relates to compositions for use in devices to freshen or scent ambient air in mechanical forced air heating, ventilating and air conditioning ("HVAC") systems and to processes for scenting air utilizing such devices.

2. Description of Related Art

The use of air scenting or freshening devices has long been known for use in releasing fragrances of various types in ambient air. Such devices have been used successfully for purposes of scenting and/or freshening air in confined spaces, particularly to mask odors such as may occur in the form of cooking odors, pet odors, tobacco smoke and the like. Furthermore, such devices have been adapted for use in mechanical HVAC systems wherein air is circulated within an interior space.

Numerous prior art air scenting/freshening devices, systems and compositions are described in the following exemplary U.S. patents. For example, U.S. Pat. No. 2,871,526 describes an air odor control system including an odor control composition positioned in a porous container for dispensing vapors to control odors. U.S. Pat. No. 4,065,262 describes an air freshening apparatus utilizing an air filter element having a plurality of containers positioned in the air filter for holding an air freshening composition. U.S. Pat. No. 4,102,656 describes an odor conditioning apparatus including a filter element positioned to be dipped into a reservoir containing a liquid which will wick into the filter to be vaporized into the environment.

U.S. Pat. No. 4,118,226 describes an air freshening device wherein a solid aromatic medium is positioned in a perforated case which, in turn, is placed in a ventilating system. U.S. Pat. No. 4,604,114 similarly describes placing large solid rods of fragrant scented material in an air circulation system. Additionally, U.S. Pat. No. 4,563,333 describes a deodorizing fitting for an air filter in which a rectangular envelope of perforated cardboard with a deodorizing insert therein is adhered to a corner of the filter; U.S. Pat. No. 4,523,870 describes an aroma dispensing cartridge placed in front of an air vent and U.S. Pat. No. 4,735,358 describes a system wherein fragrant material is placed on a tape from which the material vaporizes when the tape is run across a tape head by drive means.

It should be noted that many of the above described prior art devices disadvantageously interfere with the normal flow of air through the HVAC system. Further, none of the aforesaid devices can be readily employed in a pre-existing filter system. Rather, specifically designed frames or casings must be used to hold the fragrant structures.

In recent times a scented air freshening device has been developed which offers improved convenience and reduced air flow restriction when used with a standard filter of a type found in conventional force air ventilation systems. This device is described in U.S. Pat. Nos. 5,547,636 and 5,698,166. As shown therein, a conventional filter of the type including a porous mesh supported in a paperboard frame is fitted on its front or outwardly facing surface (i.e., the upstream surface of the filter which, when installed, faces the fan or other source of air flow in an HVAC system) with a portion of a flat porous substrate, such as an air permeable sponge material. The substrate is provided with a solution of fragrant material which may include a polymer and volatile solvent. When installed in an HVAC system, the solvent is allowed to evaporate leaving a dried fragrant polymeric residue on the substrate from which a fragrant scent is slowly released. Conveniently, the substrate may be attached to the front or outward facing surface of the air filter by the use of a simple barbed connector which pierces both the substrate and filter medium and holds the substrate in place. This device has proved to be most advantageous to homeowners who wish to use their HVAC systems to introduce and circulate a desirable fragrance throughout their homes. The device is essentially usable with any conventional furnace filter and is highly cost effective in manufacture and sale.

Other generally similar air scenting/freshening devices adapted for installation on the front or outward facing surface of a conventional air filter in an HVAC system are described in U.S. Pat. No. 5,087,273 wherein the device comprises an air permeable envelope containing aromatic beads which is positioned on the upstream or air flow facing side of the filter to provide a fragrant scent to the air circulated through the system and in U.S. Pat. No. 6,117,218 wherein the device comprises a scenting device for attachment to the upstream face of an air filter comprising a sheet formed from a material which is substantially impervious to air having a viscous liquid, such as a gel, containing a fragrance applied thereto and including openings therein through which scented air flows into and through the filter. However, each of these devices suffers from the same problems as noted above relative to the devices described in U.S. Pat. Nos. 5,547,636 and 5,698,166.

Although the above-described substrate devices have provided certain improvements over the prior art, they are not without disadvantages. Primarily, in order to use the devices effectively, the substrates must be attached to the upstream front or outward facing surface of a ventilating system filter. Attachment of these prior art substrates to the upstream surface of the filter has been necessary in order to eliminate the risk that would be presented if the substrate were to be affixed to the downstream surface of the filter. That is, if these substrates were positioned on the downstream surface, the substrate itself or disintegrated portions of the substrate could become dislodged from the downstream surface and could cause damage to the mechanical components of the HVAC system during operation. Also, the dislodged material can be directly disseminated into the environment with the HVAC air flow exiting from the filter on the downstream side thereof over extended periods of time of use. However, when the substrates of the prior art are attached to the outward facing surface of the filter to avoid this possible contamination problem, the substrates are naturally exposed to unfiltered particulate matter entrained in the ambient air entering the filter which has a tendency to cause premature blockage or clogging of the substrate and to, thereby, diminish its effectiveness of the device from releasing scented fragrance through the filter over time.

Another problem which has arisen with prior art air freshening or scenting devices arises from the volatile nature of liquid fragrances. Fragrances for scenting air typically are liquid oils. Such fragrant oils are mixtures of many different chemicals. Most of the chemicals mixed into a fragrance oil are liquids, but some components are solid. A solvent is used to dissolve the components together to form a homogenous fragrant liquid oil. The components have relatively high vapor pressures. By this is meant the fragrant liquids evaporate readily giving rise to fragrance "flash-off" problems during the manufacture of the devices. Fragrant liquid oils, therefore, are not satisfactory for use in forced air ventilation systems carrying air at significant velocities. The present invention accordingly, addresses the conflicting problems associated with the deodorizing and scenting of air in forced air ventilation systems of entraining an effective amount of scent into the air while retaining sufficient longevity of its source.

Accordingly, there exists a continuing need for a scented air freshening composition which may be used in a HVAC heating, ventilating, and cooling system for deodorizing and freshening air distributed in the system and will cause only nominal interference with the circulation of air through the system while providing sufficient scenting of the circulating air for a relatively extended predetermined period of time.

In view of the foregoing, it is a general object of the present invention to further improve over the prior art by providing a composition for use in an air scenting device and a process for scenting air circulated in an HVAC system utilizing such device.

Another object is to provide a composition for use in a device and process for freshening or scenting air in an HVAC system wherein the composition provides a strong substrate containing a volatile component which will evaporate over a relatively extended predetermined period of time to impart a desired fragrance to the surrounding environment.

A further object is to provide a device for freshening or scenting air in an HVAC system wherein a fragrant substrate is used to freshen or scent the air and wherein the substrate will not become blocked by particulate matter contained within the ambient circulated air over a relatively extended predetermined period of time of use in the system.

A still further object is to provide a composition for freshening or scenting air which is usable with a standard or conventional ventilating system air filter device and can conveniently be applied thereto either on the front or outward facing surface of the air filter or, more preferably, on the reverse or inward facing surface of the filter so that only filtered air will impinge thereon.

Still another object is to provide a device for scenting or freshening air which is convenient for use and which is highly cost-effective and efficient to implement.

These and other objects will become apparent hereinafter to those skilled in the art.

SUMMARY OF THE INVENTION

We have found that the above stated objects as well as further improvements over the prior art may be achieved utilizing a device formed by adhering a heat stable, semi-permeable gel composition to an element within an HVAC system, preferably an air filter, so as to impart an air freshening scent or fragrance to air circulating in the system over an extended period of time. Preferably, the semi-permeable gel composition is applied to a single face of an air filter at several distinct locations about the surface thereof although the gel may be applied at multiple positions on both the upstream and downstream faces of the filter simultaneously or as a single entity on either the upstream or the downstream face or both faces of the filter. Additionally, the gel composition may be applied to a filter in any selected pattern such as a dotted pattern, a random pattern, ribbon-like strips and the like so that air passing through the filter in an HVAC system will pass through the semi-permeable gel composition as well as the filter.

Thus, in one aspect, the present invention is directed to an air scenting or freshening composition comprising a thermoplastic, semi-permeable polymeric gel having a fragrance material incorporated therein. This composition is formulated for application to a filter in an HVAC system to provide an air freshening scent to air passing through the filter by dispersing scented, volatile components into the air over a predetermined period of time.

In a further aspect, the present invention provides a process for scenting air in a forced air HVAC system including a mechanical source for circulating ambient air. The process comprises providing a filter member including an air permeable filter medium and applying a scented thermoplastic, semi-permeable polymeric gel composition directly onto a face of the permeable filter medium. The filter member having the gel composition applied on the face of the filter medium is positioned in an HVAC system so that the ambient air circulated by the mechanical source contacts the gel composition on the permeable filter medium and disperses scented, volatile components from the gel composition into the circulating ambient air.

In a still further aspect of this invention, a device for scenting air in a forced air HVAC system is provided including a mechanical source of air flow for circulating ambient air through the system. The device comprises a filter supported in a frame within the HVAC system including an air permeable filter medium having an upstream facing surface and a downstream facing surface with the ambient air circulating in the system passing through the filter medium in a direction from the upstream facing surface of the filter medium to the downstream facing surface. A scented gel composition is applied on the downstream facing surface of the filter medium whereby the circulating air initially contacts the scented gel composition only after the circulating air has passed through the filter medium and any dust particles in the circulating air have been filtered out. Then, the filtered, cleaned air passes through the gel composition to scent the air circulating in the system downstream of the filter.

Accordingly, the present invention offers a number of significant advantages over the prior art. For example, the gel composition is formulated to adhere securely to the downstream inwardly facing surface of the filter medium and, therefore, the gel is exposed only to filtered air which enables increased air scenting or freshening effectiveness over a relatively long predetermined period of time. Also, the gel composition is formulated so that it is heat stable and disperses scented, volatile components into the circulating ambient air over relatively long predetermined period of time. In addition, the gel composition may be efficiently packaged for distribution in a flexible container, for example, in a tube form, to be easily and effectively dispensed onto the filter by extruding the gel from the container in any specified amount depending on the desired degree of air scenting or freshening.

BRIEF DESCRIPTION OF THE DRAWINGS

The foregoing and other novel features and advantages of the invention will be better understood upon a reading of the following detailed description taken in conjunction with the accompanying drawing wherein.

DETAILED DESCRIPTION OF A PREFERRED EMBODIMENT OF THE INVENTION

Figure 1:
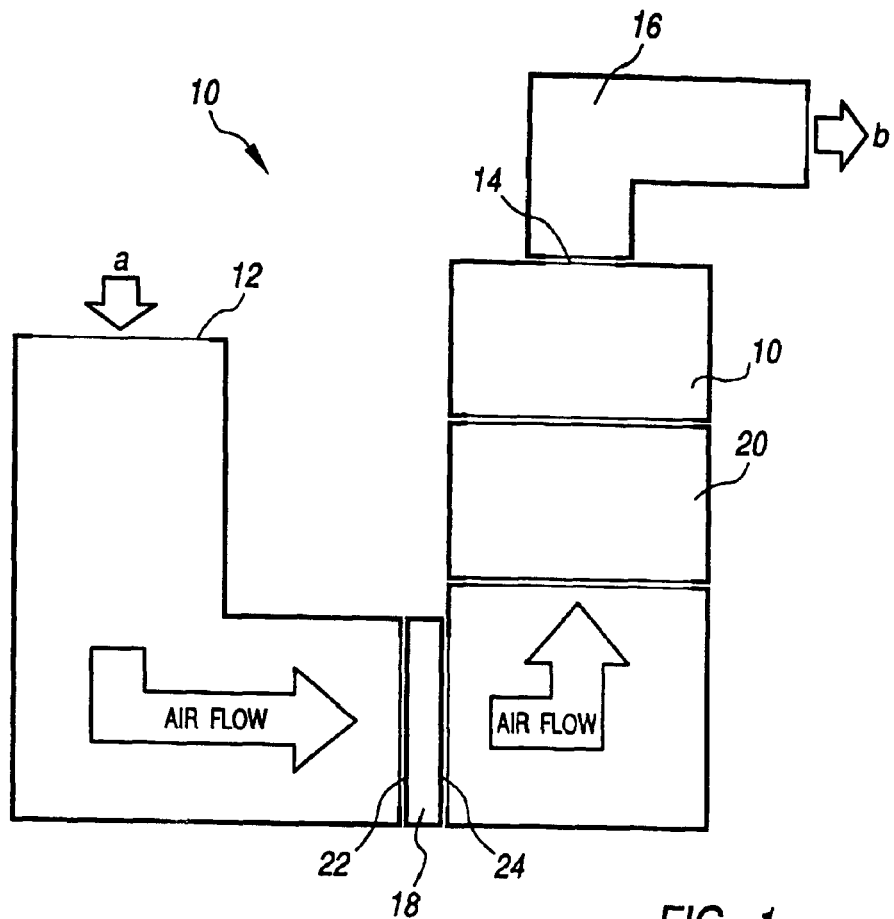
FIG. 1 is a schematic view of a standard forced air HVAC system.

An air freshening or scenting composition for use in the present invention comprises a gel formed from a blend or dispersion of a fragrant material and a thermoplastic polymer dissolved in a suitable solvent such as water, mineral oils, napthenic, paraffinic and aromatic oil blends such as those sold by Shell Inc. under the tradename Shellflex 6371 and the like. In the formulation, the thermoplastic polymeric constituent of the blend or dispersion acts as a gelling agent to promote formation of the gel composition. The resulting formulation containing the polymeric gel blended with the fragrant material enables control of the release of the fragrant material in such a way that the perception of the quality of the fragrant material remains consistent during the period of use. In this regard, a gel composition in accordance with the present invention is formulated to control the duration as well as the intensity of the release of fragrant material when the gel is installed in an HVAC system, for example, by adjusting the amount of the gel that is introduced into the system.

The gel composition may be packaged in any suitable container or package, it is preferred to package the gel in a toothpaste-type tube or other suitable flexible container for ease of application onto a suitable surface in an HVAC system such as the surface of an air filter in such a forced air heating, cooling and ventilating systems by extrusion from the flexible packaging. In this regard, a gel compositions of the present invention is formulated for application to a suitable surface in an HVAC system by any convenient method such as troweling it onto the designated surface. However, in a preferred embodiment, the gel is to formulated to be packaged and extruded from a flexible package similar to a toothpaste tube. Using this method the amount of gel can be more accurately controlled. Twenty to thirty grams of gel applied to the surface of an air filter in an HVAC system has been found to be sufficient to provide a pleasant and lasting aroma to most ventilating systems if the gel is uniformly dispersed. This amount of gel can be conveniently extruded onto a surface in the system (preferably onto the filter) through an orifice in the tube-like package ranging from about 5 mm to about 120 mm.

In assembly, the fragrance diffuses from a gel of this invention to provide scent to the ambient surroundings. Thus, the process of the present invention produces an air freshening system capable of deodorizing or imparting fragrance to air in a forced air HVAC system when the gel composition of this invention is introduced into the system by application to a part of the ventilating system, preferably the filter and, most preferably, the downstream face of the filter. The process comprises the steps of forming a dispersion of a fragrant material in a flexible, adhesive, permeable polymer. The dispersion preferably is applied to the ventilating system by extruding the gel out of a flexible package through an orifice in a location that allows the airflow to pass over and around it. The fragrant material is slowly released and deodorizes, freshens and scents the air passing through the system.

In a most preferred embodiment of this invention, the semi-permeable gel composition of this invention is adhered to a downstream or inwardly facing surface of an air filter (i.e., the face of the filter which is positioned opposite to the face which is in direct contact with the air flowing from a mechanical source of air flow such as a fan or blower) in an HVAC system. However, it should be noted that the gel composition may be applied to any surface within the system so long as air flowing in the system will impinge on the surface of the composition and will pass through the semi-permeable structure of the gel whereby the scent is distributed to the ambient surroundings.

Referring now to the drawings, FIG. 1 illustrates a conventional forced air heating, ventilating and air conditioning ("HVAC") system wherein an HVAC housing indicated generally by the reference numeral 10 has an ambient air inlet end 12 and an outlet end 14 connected to an air outlet ducting 16 which disperses filtered air into the surrounding environment. Mounted in the housing 10 is a filter 18 and a fan or blower assembly 20 for controlling the ambient air flow through the housing 10 in the direction indicated by arrows a and b from the inlet end 12 of the housing through the filter 18 from the filter's upstream facing surface 22 to its downstream facing surface 24 and then to outlet end 14 of the housing 10 and into the air outlet ducting 16 for distribution into the surrounding environment.

Figure 2:
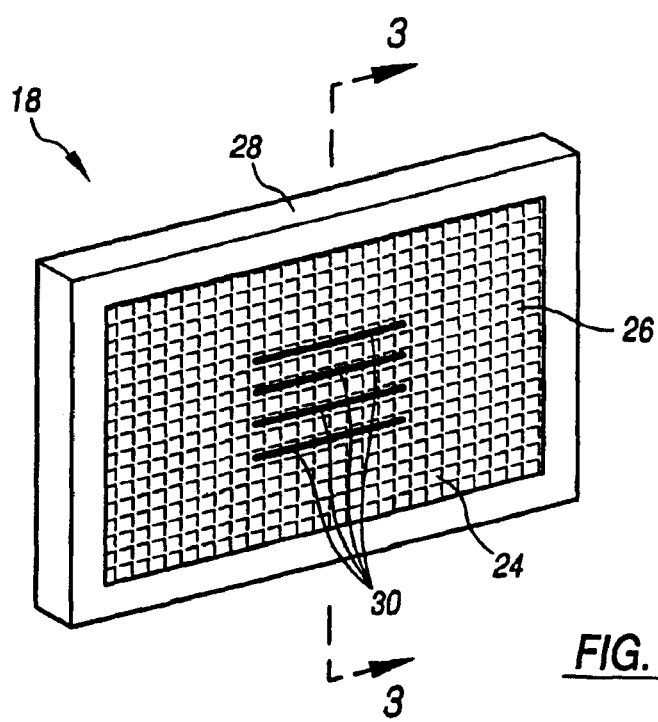
FIG. 2 is an enlarged isometric view of the air filter used in the forced air HVAC system of FIG. 1 having a novel gel composition applied to an air permeable surface thereof.
Figure 3:
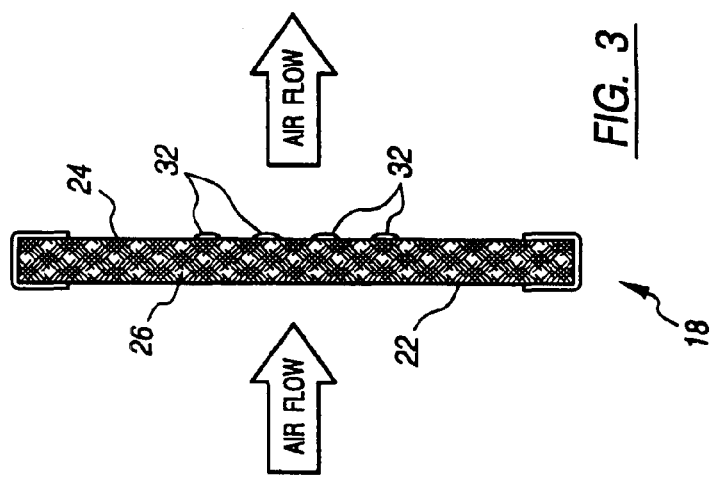
FIG. 3 is an enlarged cross-sectional of the filter illustrated in FIG. 2 taken along lines 3—3.

FIGS. 2 and 3 show a heretofore standard air filter 18 of a commercially available type typically provided for use in an HVAC system such as that depicted in FIG. 1. The filter 18 in conventional form is comprised of a fibrous air permeable filter medium 26, such as a textile material, fiberglass or other woven fibers that arrest particles in the interstices of the medium 26. Typically a suitable rigid or semi-rigid frame 28 surrounds the periphery of the filter medium 26 for holding the medium 26 in position.

As illustrated in FIGS. 2 and 3, multiple lines or strips 30 of a scented thermoplastic, semi-permeable polymeric gel 32 of the present invention are applied directly onto the filter medium 26. In this regard, it should be noted that the gel 32 can be applied in essentially any configuration as is convenient for application including ribbons, beads, dots and the like in addition to the illustrated lines or strips 30. Furthermore, in practice, the application of gel 32 is preferably concentrated around a central portion of the filter medium 26 as shown in FIGS. 2 and 3.

In accordance with the present invention, the gel 32 is preferably applied to a single face of the filter 18, and most preferably, to the downstream or inwardly facing surface 24 of the filter 18, as illustrated in FIGS. 2 and 3. In this manner, the gel 32 is not exposed to unfiltered airborne dust particles and other impurities present in the ambient air drawn into the HVAC housing 10 through the inlet end 12 by the operation of fan or blower assembly 20 as illustrated in FIG. 1. As best illustrated in FIG. 3, the circulating air impacts the upstream surface 22 of the filter 18 and passes through the filter medium 26 whereby airborne dust particles and other impurities in the ambient air which would tend to blind or block the gel 32 and diminish its effectiveness are filtered out of the air flow before the circulating air initially contacts the gel 32 on the downstream surface 24 of the filter 18.

Figure 4:
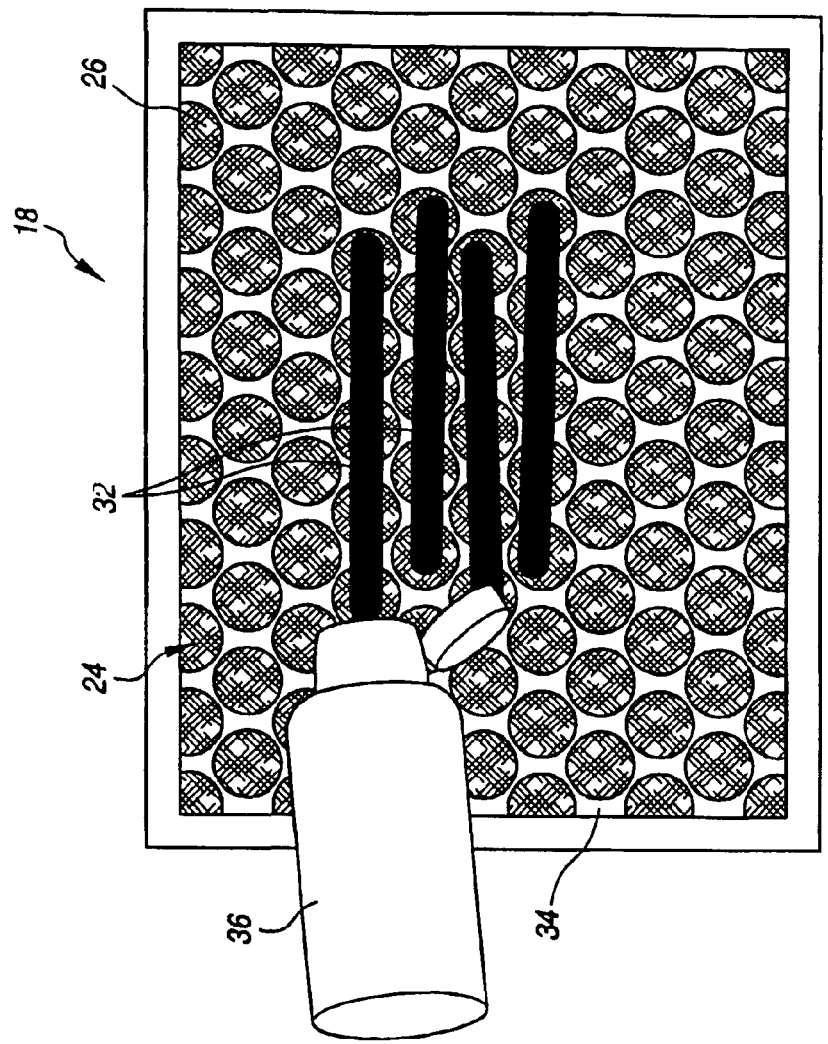
FIG. 4 is a perspective view illustrating application of a gel composition of the present invention from a flexible container onto a surface of a filter.

FIG. 4 illustrates another typical form of a filter 18 having a mesh screen 34 attached to the frame 28 for further maintaining the filter medium 26 within the frame 28. In normal practice and as illustrated, the screen 34 is affixed on the downstream surface 24 of the filter 18. FIG. 4 further shows the gel 32 being applied to the filter 18 from a flexible tube or dispenser 36 as can be accomplished by squeezing the flexible container and extruding the gel out of the tube 36 and onto the filter 18 in a manner similar to the squeezing of toothpaste from a tube of toothpaste. Thus, the gel 32 may in preferred form be dispensed from the flexible dispenser, container or tube 36, as illustrated in FIG. 4, which may be squeezed to extrude the gel 32 therefrom in the preferred lined or striped configuration or in any other suitable fashion such as ribbons, beads, dots and the like. Furthermore, as illustrated in FIG. 4, in a preferred embodiment, the gel 32 is applied directly onto the surface of the filter medium 26 and, also, for convenience, it is applied from the flexible tube 36 onto mesh screen 34 on the downstream surface of the filter.

While many forms of scented gel 32 may be used in the present invention, in a preferred embodiment, a gel composition is provided which releases fragrant material, under typical household conditions, for a predetermined period of time ranging from about one day to several months or more, with a most preferred period being about thirty days. In a further preferred embodiment of this invention, the gel composition is formulated in a manner such that the resulting gel presents a uniform and pleasing appearance in order to expedite packaging of the gel in a transparent container.

Air freshening or scenting compositions for use in the present invention may be prepared by a process comprising forming a solution of a thermoplastic polymer in a suitable solvent such as water, mineral oils and the like, and blending or dispersing a fragrant component in the polymeric solution thereby producing a semi-permeable gel composition. Exemplary of suitable thermoplastic polymers for use in forming the semi-permeable gels of the present invention are hydrogenated styrene/isoprene copolymers such as those sold by Shell Inc. under the trade names Krayton G1652 and Krayton G165; volatile silicones such as dimethicone which is known variously in the art as dimethyl polysiloxane, dimeticon, polydimethylsiloxane and α-(trimethylsilyl)-ω-methylpoly[oxy-(dimethylsilylene)] as sold by Dow Corning under the trade name 344 Fluid; polyacrylic acids such as those sold by B.F. Goodrich Inc. under the trade name Carbomer 941 and the like.

In particular, we have found that it is highly beneficial in producing a polymeric gel for use in the present invention to employ a volatile solvent, such as dimethicone, which quickly volatilizes after extrusion leaving a more crosslinked and non-tacky gel bead surface. This more crosslinked surface is less permeable and aids in regulating fragrance diffusion from the gel matrix which is formed thereby enabling the resulting composition to slowly release its scenting or aroma changing components for an extended period of time, for example, 30 days.

With regard to fragrance materials suitable for use in the semi-permeable air freshening gel compositions of the present invention, it should be noted that any desirable known scenting or fragrance types may be employed to produce such compositions provided that the fragrance is compatible with the gel and the formulas are balanced to eliminate partial fractionation. Examples of scents or fragrances for use in producing the gel compositions of the present invention include, but are not limited to, vanilla fragrances such as those sold under the designation 100J93 by Flavor & Fragrance Specialties, Inc.; floral fragrances such as those sold under the designation 100D56 by Flavor & Fragrance Specialties, Inc.; citrus fragrances such as those sold under the designation 200K89 by Flavor & Fragrance Specialties, Inc. and the like.

Although most fragrances are bactericidal, we have found that in formulating the gel compositions of the present invention it may be desirable to incorporate a suitable preservative or microbiocide in the blend or dispersion to discourage the growth of microorganisms that may adversely affect the odor or stability of the gel. Examples of suitable preservative/microbiocidal agents for use herein are diazolidinyl urea, propyl paraben and methyl paraben compositions such as those sold by Sutton Laboratories Inc. under the trade name Germaben II. Other preservative/microbiocidal agents which have proven to be effective for use herein are hydrogen peroxide, sodium benzoate and the like.

We have found that the rate of release of the fragrance from the gel composition can be controlled by varying the concentration of the polymers and/or gelling agents therein. Furthermore, we have found that the rate of release of fragrance can be further affected by incorporating a co-solvent such as diethyl phthalate in the polymeric blend or dispersion. The use of a co-solvent has been found to assist in the movement of the fragrance through the gel matrix formed in the compositions of the present invention. In addition to diethyl phthalate, other co-solvent compounds which have been found to be suitable for use in preparing the gel compositions of this invention include triethyl acetate, dipropylene glycol, ethyl alcohol, benzyl benzoate and dioctyl adipate. However, diethyl phthalate is preferred because it is a very good solvent for fragrance ingredients and assists in developing the clarity of the gel system.

A preferred surfactant for use in preparing the gel compositions of this invention is a nonionic, ethoxylated alkyl phenol such as surfactant product sold by Rohm and Haas under the trade name Triton X-100. Other surfactants such as nonyl phenols and ethoxylated alcohol may also be used. The surfactant should have a low odor profile so that it will not interfere with the odor profile of the fragrance. Exemplary of suitable surfactants which also may be used herein are Octoxynol 9; Nonoxynol-6 sold by Texaco under the tradename Surfonic N60; Nonoxynol-9 sold by Rhodia Inc. under the tradename Igepal CO630; Nonoxynol 10 sold by Union Carbide under the tradename Tergitol NP-10; Polysorbate 20 sold by Uniqema America under the tradename Tween 20; Ceteth 2 sold by Uniqema America under the tradename Bry 72; Steareth-20 sold by Uniqema America under the tradename Bry 78. Surfactants may also be added to the gel compositions of this invention to improve clarity, to control the rate of evaporation and/or to aid in the dispersion of the fragrance.

Furthermore, the gel may include a coloring agent and/or a glitter therein to further enhance its commercial appeal. Still further, the polymeric constituent of the blend or dispersion should be selected to have low toxicity and flammability so that it is suited for household use. The gel may also contain preservatives or biocides to avoid growth of microorganisms that can adversely affect the appearance of the gel and antioxidants to prevent degradation of the ingredients in the gel. Antiblaze materials such as Antiblaze 140 sold by Albright & Wilson Inc. may also be added as a flame retardant in the composition. Furthermore, an aversive agent such as denatonium benzoate may be present in the formulation to discourage ingestion of the gel by users thereof.

The gel formed from the polymeric blend or dispersion of this invention must be adhesive so that it will adhere effectively to the filter or to other parts of the ventilating system. The gel should also have a viscosity such that it can be easily extruded from a flexible container and the viscosity of the gel should not vary significantly throughout the temperature range of anticipated use and storage, which normally would range from about 40° F. to about 150° F., so that the gel will not run off the surface to which it is applied nor release the fragrant components too quickly or too slowly. Preferably, the viscosity of the gel should be in a range of about 2,000 centipoise to about 500,000 centipoise over the temperature range of about 40° F. to about 150° F., most preferably, in a range of about 2,000 centipoise to about 50,000 centipoise over such temperature range. In addition, the gel must not form an impermeable film on the surface to which it is applied. To the contrary, a gel composition in accordance with the present invention must be sufficiently permeable to release the fragrant material in the blend or dispersion at a uniform rate without perceptible alteration of the quality of the fragrant material after the gel is introduced into an HVAC system. This degree of permeability is referred to herein as being semi-permeable.

A preferred process of making an air freshener of this type is to create a gel of thermoplastic elastomers dissolved in mineral oil. The concentration of the elastomer may vary from 1.0% to 30%. The concentration is dependent upon the composition of the fragrance, the desired viscosity and the rate of release of the fragrance. A fragrance is dispersed therein at a concentration of 0.1 to 70.0%. The concentration of the fragrance is dependent upon the desired strength of the aroma of the finished product as well as upon the strength and composition of the fragrance. Some fragrance ingredients have the effect of reducing the viscosity of the gel so the composition and concentration of the fragrance can be critical to the strength and stability of the gel.

The gel should be packaged in a flexible container, preferably a squeezable toothpaste-like tubular container, so that it can be easily extruded by the user in the form of strips. Another convenient container is a PETG Tottle Bottle made by Fenton, Weber and Jones Packaging, Inc. It is very useful when the cap has an orifice of 10 mm.

The following examples are intended for illustration purposes only, and should not be deemed to limit the scope of the invention as defined in the appended claims.

EXAMPLE 1

A transparent gel composition in accordance with the present invention having a vanilla scent was prepared in the laboratory employing the following process:

10 grams of Krayton G1652 and 3 grams of Krayton G4609 (hydrogenated styrene/isoprene copolymers sold by Shell Inc) were dispersed in 53 grams of Shellflex 6371, a blend of napthenic, paraffinic and aromatic oils sold by Shell, Inc. The dispersion was heated to 195° F. with stirring until the dispersion became clear. It was then cooled to 160° F. and 10 grams of dimethicone were added and mixed until uniform. 25 grams of Vanilla fragrance (100J93 sold by Flavor & Fragrance Specialties, Inc.) were then mixed into the dispersion until the mixture formed a uniform and clear gel.

The resultant gel mixture, which had a viscosity of 30,000 centipoise, was poured into flexible tubes and capped with caps having an orifice of 10 mm. Then, four lines of the gel, each line being approximately 5 inches in length, were extruded from the tube onto the downstream facing surface of an air filter, which was then placed into an HVAC system and the air conditioner in the system was activated. The gel adhered to the filter and did not drip or run.

A strong vanilla scent was noticed immediately after the filter having the gel composition adhered thereto was placed in the system. Thereafter, the air conditioner was run continuously for 30 days. An expert panel considered the vanilla scent to be strong for the first three days, pleasant for an additional fourteen days and perceptible for remainder of the test period.

EXAMPLE 2

A gel composition in accordance with the present invention having a floral scent was prepared in the laboratory employing the following process:

5 grams of Cabosil M-5 (silica, silicone dioxides sold by Degussa Inc.) was dispersed into a blend of 20 grams of diethyl phthalate and 29.7 grams of mineral oil. The dispersion was heated to 110° F. and mixed until uniform. 10 grams of dimethicone was added and mixed until uniform. 35 grams of Floral fragrance (100D56 sold by Flavor & Fragrance Specialties, Inc.) was added and the resulting gel was mixed until uniform.

0.10 grams of denatonium benzoate was incorporated in the gel as a bitter aversive agent. 0.01 grams of D&C Red #40 coloring agent was also included and 0.2 grams of a preservative/microbiocidal agent Germaben III (a diazolidinyl urea, propyl paraben and methyl paraben compositions sold by Sutton Laboratories Inc.) was added and mixed until the color of the gel was uniform.

The resultant gel mixture, which had a viscosity of 40,000 centipoise, was poured into flexible tubes and capped with caps having an orifice of 10 mm. Then, four lines of the gel, each line being approximately 5 inches in length, were extruded from the tube onto the downstream facing surface of an air filter, which was then placed into an HVAC system and the air conditioner in the system was activated. The gel adhered to the filter and did not drip or run. A strong floral odor was immediately noticed. The air conditioner was run continuously for 30 days. An expert panel considered the floral odor strong for five days, pleasant for an additional sixteen days and perceptible for the remainder of the test period.

In a further test, four lines of the gel, each line being approximately 12 inches in length and weighing a total of 23 grams, were extruded onto a filter medium of an air filter and the filter having the gel composition adhered thereto was placed into the HVAC system and the air conditioner activated. The gel adhered to the filter and did not drip or run. A strong floral odor was immediately noticed. The air conditioner was run continuously for 30 days. An expert panel considered the floral odor strong for five days, pleasant for an additional sixteen days and perceptible for the remainder of the test period.

EXAMPLE 3

An opaque gel composition in accordance with the present invention having a citrus scent was prepared in the laboratory employing the following process:

3 grams of polyacrylic acid (sold by B.F. Goodrich, Inc. under the tradename Carbomer 941) was mixed in 40 grams of propylene glycol and heated to 150° F. until completely dispersed. The mixture was cooled to 100° F. and 20 grams of Citrus fragrance (200K89 sold by Flavor & Fragrance Specialties, Inc.) were added and mixed until a uniform gel formed. 20 grams of a surfactant (Triton X100 sold by Union Carbide Corporation) were added and mixed until uniform.

Separately, 0.1 grams of a methylchloroisothiazolinone and methlisothiazolin preservative (sold under the tradename Kathon CGICP) and 2 grams of triethanolamine were dissolved in 14.9 grams of water to form a solution. This solution was then added to the above mixture and mixed until uniform.

The resultant gel mixture, which had a viscosity of 25,000 centipoise, was poured into flexible tubes and capped with caps having an orifice of 10 mm. Then, four lines of the gel, each line being approximately 5 inches in length, were extruded from the tube onto the downstream facing surface of an air filter, which was then placed into an HVAC system and the air conditioner in the system was activated. The gel adhered to the filter and did not drip or run. A strong citrus odor was noticed immediately. The air conditioner was run continuously for 30 days. An expert panel considered the citrus odor strong for five days, pleasant for 12 days and perceptible for the remainder of the test period.

While the present invention has been described in connection with a preferred embodiment, it will be apparent to those skilled in the art that many changes and modifications may be made without departing from the true spirit and scope of the invention. Accordingly, it is intended by the appended claims to cover all such changes and modifications as come within the spirit and scope of the invention.

What is claimed is:

1. An HVAC system including:
   a) an air freshening composition comprising a thermoplastic, semi-permeable polymeric gel having a fragrance material incorporated therein,
   b) a filter member including an air permeable filter medium:
   c) the polymeric gel containing a polymeric gelling agent selected from the group consisting of hydrogenated styrene/isoprene copolymers; volatile silicones; polyacrylic acids and mixtures thereof and being formulated to adhere directly on a surface of the filter member, the gel having sufficient viscosity at temperatures in the range of about 40° F. to about 150° F. to prevent run off of the gel from the surface of the filter to which it is adhered and to enable effective release of scented, volatile components in the fragrance material to provide an air freshening scent to air passing through the filter by dispersing the scented, volatile components into the air over a predetermined period of time.

2. The HVAC system of claim 1 wherein the polymeric gel contains about 1 weight percent to about 30 weight percent of the polymeric gelling agent.

3. The HVAC system of claim 2 wherein the polymeric gel contains about 0.1 weight percent to 70 weight percent of the fragrance material.

4. The HVAC system of claim 3 wherein the air freshening composition contains about 0–0.1 weight percent of an aversive agent and about 0 to 50 weight percent of a surfactant.

5. The HVAC system of claim 1 wherein the air freshening composition contains about 0–50 weight percent of a co-solvent.

6. The HVAC system of claim 5 wherein the co-solvent is selected from the group consisting of diethyl phthalate; triethyl acetate, dipropylene glycol, ethyl alcohol, benzyl benzoate, diooctyl adipate and mixtures thereof.

7. The HVAC system of claim 6 wherein the air freshening composition contains about 0–5 weight percent of a material selected from the group consisting of color agents, glitter and mixtures thereof.

8. The HVAC system according to claim 1, in which the viscosity of the gel is in a range of about 2,000 centipoise to about 500,000 centipoise over a temperature range of about 40° F. to about 150° F.

9. The HVAC system of claim 1 wherein the predetermined period of time ranges from about one day to several months.

10. A process for scenting air in a forced air HVAC system including a mechanical source for circulating ambient air comprising:
   a) providing a filter member including an air permeable filter medium;
   b) adhering a scented thermoplastic, semi-permeable polymeric gel composition directly onto a surface of the permeable filter medium; the polymeric gel composition containing a polymeric gelling agent selected from the group consisting of hydrogenated styrene/isoprene copolymers; volatile silicones; polyacrylic acids and mixtures thereof and having a fragrance material incorporated therein, the polymeric gel having sufficient viscosity at temperatures in the range of about 40° F. to about 150° F. to prevent run off of the gel from the surface of the filter to which it is adhered and to enable effective release of scented, volatile components in the fragrance material; and
   c) positioning the filter member having the gel composition adhered to the surface of the filter medium in an HVAC system so that the ambient air circulated by the mechanical source contacts the gel composition on the permeable filter medium and disperses the scented, volatile components from the gel composition into the circulating ambient air.

11. The process of claim 10 wherein the filter medium has an upstream facing surface and a downstream facing surface with the ambient air circulating in the HVAC system passing through the filter medium in a direction from the upstream facing surface of the filter medium to the downstream facing surface and the semi-permeable gel composition is adhered to the downstream facing surface of the filter.

12. The process of claim 10 wherein the semi-permeable gel composition contains about 1 weight percent to about 30 weight percent of the polymeric gelling agent.

13. The process of claim 10 wherein the polymeric gel contains about 0.1 weight percent to 70 weight percent of the fragrance material.

14. The process of claim 10 wherein the polymeric gel contains about 0–0.1 weight percent of an aversive agent and about 0 to 50 weight percent of a surfactant.

15. The process of claim 10 wherein the polymeric gel contains about 0–50 weight percent of a co-solvent.

16. The process of claim 15 wherein the co-solvent is selected from the group consisting of diethyl phthalate; triethyl acetate, dipropylene glycol, ethyl alcohol, benzyl benzoate, diooctyl adipate and mixtures thereof.

17. The process of claim 10 wherein the polymeric gel contains about 0–5 weight percent of a coloring agent.

18. The process of claim 10 wherein the viscosity of the polymeric gel is in a range of about 2,000 centipoise to about 500,000 centipoise over a temperature range of about 40° F. to about 150° F.

19. A device for scenting air in a forced air HVAC system including a mechanical source of air flow for circulating ambient air through the system comprising:
   a filter supported in a frame within the HVAC system including an air permeable filter medium having an upstream facing surface and a downstream facing surface with the ambient air circulating in the system passing through the filter medium in a direction from the upstream facing surface of the filter medium to the downstream facing surface; and
   a scented gel composition adhered directly on the downstream facing surface of the filter medium whereby the circulating air initially contacts the scented gel composition after the circulating air has passed through the filter medium and the air passes through the gel composition to scent the air circulating in the system downstream of the filter; the gel composition comprising a thermoplastic, semi-permeable polymeric gel containing a polymeric gelling agent selected from the group consisting of hydrogenated styrene/isoprene copolymers: volatile silicones; polyacrylic acids and mixtures thereof and having a fragrance material incorporated therein, the polymeric gel having sufficient viscosity at temperatures in the range of about 40° F. to about 150° F. to prevent run off of the gel from the surface of the filter to which it is adhered and to enable effective release of scented, volatile components in the fragrance material to provide an air freshening scent to air passing through the filter by dispersing the scented, volatile components into the air over a predetermined period of time.

20. The device of claim 19 wherein the polymeric gel composition contains about 1 weight percent to about 30 weight percent of a polymeric gelling agent.

21. The device of claim 19 wherein the polymeric gel contains about 0.1 weight percent to 70 weight percent of the fragrance material.

22. The device of claim 19 wherein the polymeric gel contains about 0–0.1 weight percent of an aversive agent and about 0 to 50 weight percent of a surfactant.

23. The device of claim 19 wherein the polymeric gel contains about 0–50 weight percent of a co-solvent.

24. The device of claim 23 wherein the co-solvent is selected from the group consisting of diethyl phthalate; triethyl acetate, dipropylene glycol, ethyl alcohol, benzyl benzoate, diooctyl adipate and mixtures thereof.

25. The device of claim 19 wherein the polymeric gel contains about 0–5 weight percent of a coloring agent.

26. The device of claim 19 wherein the viscosity of the polymeric gel is in a range of about 2,000 centipoise to about 500,000 centipoise over a temperature range of about 40° F. to about 150° F.

* * * * *